US009555109B2

(12) United States Patent
Bogdanov et al.

(10) Patent No.: US 9,555,109 B2
(45) Date of Patent: Jan. 31, 2017

(54) METHOD OF INHIBITING CELL PROLIFERATION INDUCED BY ALTERNATIVELY SPLICED TISSUE FACTOR BY ADMINISTERING A MONOCLONAL ANTIBODY

(71) Applicant: The University of Cincinnati, Cincinnati, OH (US)

(72) Inventors: Vladimir Bogdanov, Cincinnati, OH (US); Henri Versteeg, Utrecht (NL)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 13/747,405

(22) Filed: Jan. 22, 2013

(65) Prior Publication Data

US 2013/0189276 A1 Jul. 25, 2013

Related U.S. Application Data

(60) Provisional application No. 61/588,724, filed on Jan. 20, 2012.

(51) Int. Cl.

*A61K 39/395* (2006.01)
*C07K 16/36* (2006.01)
*A61K 38/02* (2006.01)
*A61K 31/7088* (2006.01)
*A61K 39/00* (2006.01)

(52) U.S. Cl.

CPC ..... *A61K 39/39558* (2013.01); *A61K 31/7088* (2013.01); *A61K 38/02* (2013.01); *C07K 16/36* (2013.01); *A61K 2039/505* (2013.01); *C07K 2317/76* (2013.01)

(58) Field of Classification Search

None

See application file for complete search history.

(56) References Cited

U.S. PATENT DOCUMENTS 7,045,350 B2 5/2006 Nemerson et al.

FOREIGN PATENT DOCUMENTS

| | | | | |
|---|---|---|---|---|
| WO | WO2008054822 | * | 5/2008 | ........... G01N 33/574 |
| WO | WO2010066803 | * | 6/2010 | ............. C07K 16/36 |

OTHER PUBLICATIONS

Signaevsky et al. Role of alternatively spliced Tissue Factor in pancreatic cancer growth and angiogenesis. Semin. Thromb. Hemost. 34, 161-169, 2008.* van den Berg et al., Alternatively spliced and full-length tissue factor reveal a non-identical relationship to clinicopathological parameters in a large cohort of human breast cancer. J Thromb. Haemost. 9 (Suppl. 2) p. 803, 2011.*

Hobbs et al.. Alternatively spliced human tissue factor promotes tumor growth and angiogenesis in a pancreatic cancer tumor model. Thromb. Res., 120 (Suppl. 2), S13-S21, 2007.*

Reddehase et al. A pentapeptide as minimal antigenic determinant for MHC class I-restricted T lymphocytes, Nature, 337, 651-653, 1989.*

Van Den Berg, Y.W., et al., Alternatively Spliced Tissue Factor Induces Angiogenesis Through Integrin Ligation, PNAS Early Eedition, Medical Sciences, www.pnas.org/cgi/doi/10.1073/pnas.0905325106 (13 pages). PNAS, 106 (46) , 19497-19502, 2009.

* cited by examiner

*Primary Examiner* — Elly-Gerald Stoica

(74) *Attorney, Agent, or Firm* — Wood Herron & Evans LLP

(57) ABSTRACT

Embodiments of the invention are directed to a method of inhibiting proliferation of a cell induced by asTF that includes exposing the proliferating cell to an inhibitor of asTF at a concentration sufficient to attenuate asTF induced proliferation. In an embodiment, the proliferating cell is a cancer cell such as a breast cancer cell. The inhibitor of asTF may be an anti-asTF antibody, such as a monoclonal antibody or an antibody fragment, a small molecule, a peptide, nucleic acid, and combinations thereof.

11 Claims, 13 Drawing Sheets vascular density (CD31+ structures/field)
40 35 30 25 20 15 10 5 0
con IgG Rb1
FIG. 5G
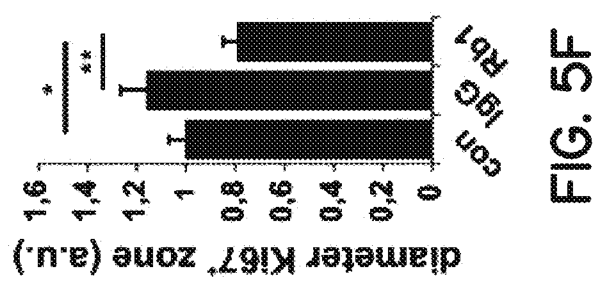
FIG. 5F
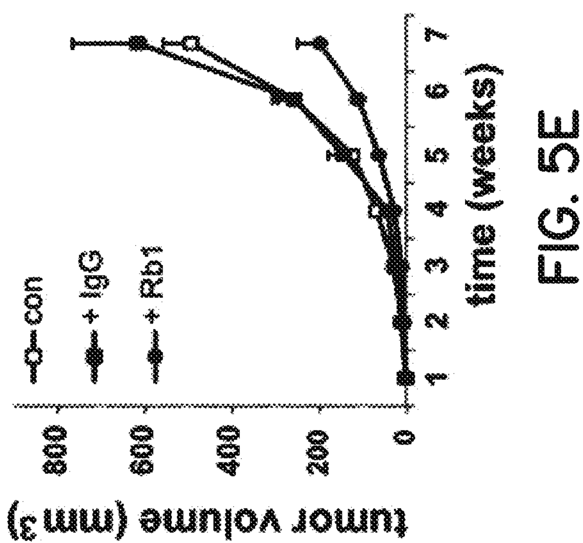
FIG. 5E
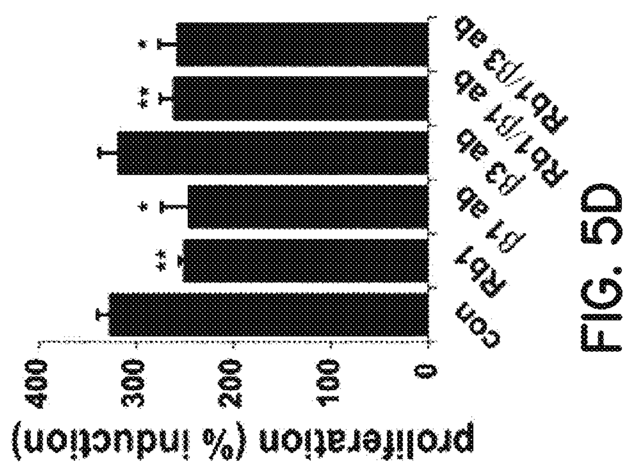
FIG. 5D

SEQUENCE LISTING

```
<160> NUMBER OF SEQ ID NOS: 3

<210> SEQ ID NO 1
<211> LENGTH: 11
<212> TYPE: PRT
<213> ORGANISM: Homo sapiens

<400> SEQUENCE: 1

Glu Trp Gly Arg Ala Gly Arg Arg Thr Pro His
1               5                   10


<210> SEQ ID NO 2
<211> LENGTH: 140
<212> TYPE: PRT
<213> ORGANISM: Unknown
<220> FEATURE:
<223> OTHER INFORMATION: rabbit

<400> SEQUENCE: 2

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Thr Tyr Asp Met Thr Trp Val Arg Gln Ala Pro Gly Lys Gly Leu Glu
    50                  55                  60

Trp Ile Gly Ile Ile Gly Ser Arg Gly Thr Thr Arg Tyr Ala Asn Trp
65                  70                  75                  80

Ala Lys Gly Gln Phe Thr Ile Ser Arg Thr Ser Thr Thr Val Asp Leu
                85                  90                  95

Lys Ile Tyr Ser Pro Thr Thr Glu Asp Thr Ala Thr Tyr Phe Cys Ala
            100                 105                 110

Arg Ser Ala Tyr Pro Ala Ser Gly Asn Phe Ile Asp Asp Gly Phe Asp
        115                 120                 125

Pro Trp Gly Pro Gly Thr Leu Val Thr Val Ser Ser
    130                 135                 140


<210> SEQ ID NO 3
<211> LENGTH: 133
```

-continued

```
<212> TYPE: PRT
<213> ORGANISM: Unknown
<220> FEATURE:
<223> OTHER INFORMATION: rabbit

<400> SEQUENCE: 3

Met Asp Thr Arg Ala Pro Thr Gln Leu Leu Gly Leu Leu Leu Leu Trp
1               5                   10                  15

Leu Pro Gly Ala Arg Cys Ala Asp Phe Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Ser Ile Tyr Ser Tyr Leu Ser Trp Tyr Gln Gln Lys Pro Gly
    50                  55                  60

Gln Pro Pro Lys Leu Leu Ile Tyr Gly Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Gln Gly Tyr Thr Tyr Thr Asp Ile Asp Asn Val Phe Gly Gly Gly Thr
        115                 120                 125

Glu Val Val Val Lys
    130
```

METHOD OF INHIBITING CELL PROLIFERATION INDUCED BY ALTERNATIVELY SPLICED TISSUE FACTOR BY ADMINISTERING A MONOCLONAL ANTIBODY

RELATED APPLICATION

The Present application claims the benefit of U.S. Provisional Application No. 61/588,724 filed Jan. 20, 2012, the disclosure of which is hereby incorporated herein by reference in its entirety.

FIELD

The present invention is directed to methods and composition for the inhibition of cell proliferation induced by alternatively spliced Tissue Factor and more particularly to method of treating cancer with inhibitors of asTF.

BACKGROUND

Full-length Tissue Factor (flTF) is the principal initiator of blood coagulation. Following vascular damage, flTF binds its ligand FVII(a) which triggers clot formation. Aside from sub-endothelial tissues, flTF is also abundant on cancer cells and fuels tumor progression by modulating major signaling pathways; flTF regulates integrin α3β1 function and cell migration, and flTF in complex with FVIIa activates Protease Activated Receptor (PAR)2, while association of flTF with β1 integrins enhances PAR2 activation. flTF-dependent PAR2 activation and integrin regulation result in the production of pro-angiogenic factors such as VEGF, CXCL1 and IL-8, thus promoting the angiogenic switch and, consequently, tumor growth in vivo.

Alternative splicing of TF pre-mRNA yields alternatively spliced TF (asTF). asTF lacks the transmembrane domain and can thus be secreted. In humans and mice, asTF contains a novel C-terminus with poor homology to any known proteins. High expression of asTF expression in tumor cell lines suggests a role in tumor progression. Subcutaneous growth of pancreatic cancer cells overexpressing asTF, results in larger and more vascularized tumors. We recently discovered that asTF induces angiogenesis, independent of PAR2 activation, by acting as an integrin ligand. Thus, flTF and asTF facilitate cellular signaling via distinct mechanisms critical to tumor cell behavior.

Alternative pre-mRNA splicing increases the repertoire of cellular proteins. In cancer cells, such as breast cancer cells, proteins that modulate splicing events such as ASF/SF2 and SRp55, are frequently upregulated and contribute to cell transformation. Breast cancer cells exhibit specific alternative splicing signatures that were proposed as potential prognostic factors in breast cancer. Alternative splicing of proteins such as spleen tyrosine kinase (Syk), p53, PTEN, CXCR3 and Rac1 impacts breast cancer cell behavior and therefore, disease progression.

Currently, nothing is known about asTF expression and function in breast cancer. Regulated splicing of TF pre-mRNA in human monocytes is controlled by several SR proteins, including ASF/SF2 and SRp55. Expression of SR proteins is frequently perturbed in breast cancer tumors, and it is thus plausible that the relative abundance of flTF and asTF is also altered in breast cancer.

SUMMARY

Prior studies that attempted to correlate Tissue Factor expression in breast cancer specimens with clinical parameters such as tumor grade and disease outcome did not discriminate between flTF and asTF. Thus, it was not known as to how the two TF isoforms associate with and contribute to breast cancer progression.

The data disclosed herein demonstrate that asTF induces proliferation in cancer cells through mechanisms independent of the blood clotting cascade and independent of angiogenesis.

Accordingly, embodiments of the invention are directed to a method of inhibiting proliferation of a cell induced by asTF that includes exposing the proliferating cell to an inhibitor of asTF at a concentration sufficient to attenuate asTF induced proliferation. In an embodiment, the proliferating cell is a cancer cell such as a breast cancer cell. The inhibitor of asTF may be an anti-asTF antibody, such as a monoclonal antibody, an antibody fragment, or a nanobody, a small molecule, a peptide, nucleic acid, and combinations thereof.

BRIEF DESCRIPTION OF THE DRAWINGS

FIG. 5D is a bar graph illustrating the effect of Rb1, β1 integrin antibody, β3 integrin antibody, combination Rb1 and β1 integrin antibody, and combination Rb1 and β3 integrin antibody.

FIG. 5E is a graph illustrating the effect of Rb1 on tumor volume.

FIG. 5F is a bar graph illustrating the effect of Rb1 on macrophage infiltration into tumor.

FIG. 5G is a bar graph illustrating the effect of Rb1 on vascular density of tumor.

DETAILED DESCRIPTION

Figure 1B:
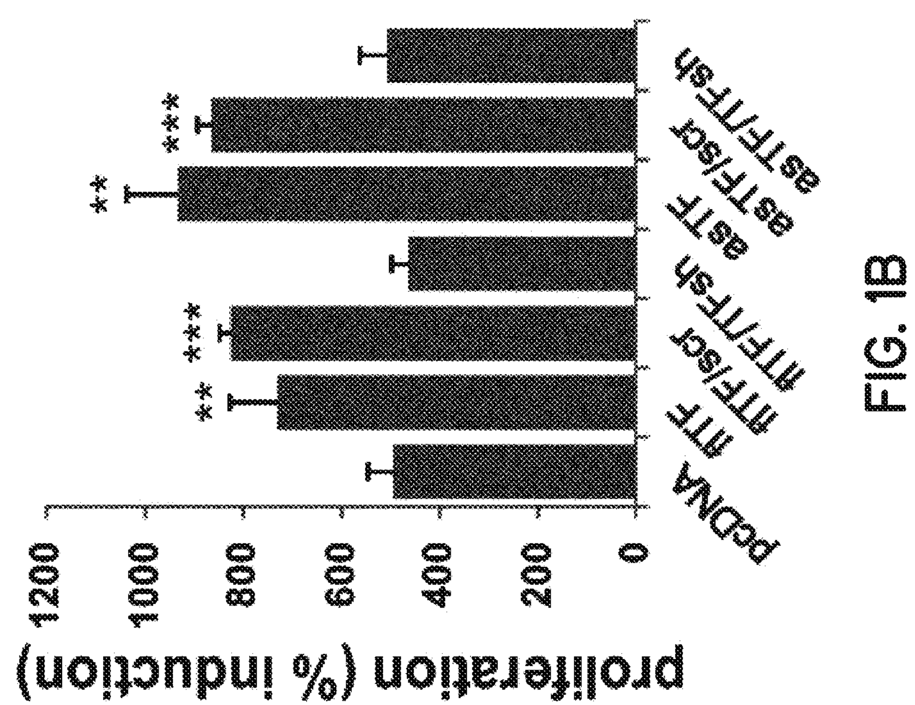
FIG. 1B is bar graph illustrating asTF induced cell proliferation.

Prior studies pointed to a potentiating role for TF in tumor progression; however, the specific role of asTF in tumor progression was not previously understood. Prior research indicated an effect of asTF on tumor induced-angiogenesis through one or both of the thrombin generation-based clotting cascade or binding of integrin receptors. The latter process involves the non-proteolytic effects of asTF. Previous studies failed to appreciate the non-proteolytic autocrine effect of asTF on cell proliferation such as occurs with cancer progression. Described herein are data demonstrating the autocrine effect of asTF to promote cellular proliferation and that blockade of the autocrine effect of asTF attenuates cellular proliferation independent of previously understood pathways. Thus, one aspect of the present invention is directed to a method of inhibiting cell proliferation induced by the autocrine effects of asTF by attenuating asTF activity. Such cancers comprise solid tissue cancers e.g. breast, lung, cervical, urogenital, kidney, prostate, and gastrointestinal e.g pancreatic cancer (pancreatic ductal adenocarcinoma and other forms of malignancy of the pancreas), esophagus, stomach, liver, and colorectal cancer; melanoma; glioma; hematologic cancers such as acute promyelocytic/myelogenous leukemia.

Another aspect of the invention is directed to the treatment of cell proliferation in a subject, such as cancer, with a composition that attenuates asTF activity. An exemplary cancer is breast cancer but other cancers wherein asTF is produced at levels at least two times the level of tissue from which the cancer originates may be treated as well.

In one embodiment of the methods described herein, asTF activity is attenuated with a composition that interacts with asTF. An exemplary compound that interacts with asTF is an anti-asTF antibody. One such anti-asTF antibody is a monoclonal antibody raised against the extreme C-terminal peptide sequence unique to human asTF (EWGRAGRRTPH (SEQ ID NO:1)). Another such anti-asTF antibody includes the following variable sequences:

(SEQ ID NO: 2)
```
METGLRWLLLVAVLKGVQCQSVEESGGRLVTPGTPLTLTC

TASGFSLSTYDMTWVRQAPGKGLEWIGIIGSRGTTRYANW

AKGQFTISRTSTTVDLKIYSPTTEDTATYFCARSAYPASG

NFIDDGFDPWGPGTLVTVSS
```
and (SEQ ID NO: 3)
```
MDTRAPTQLLGLLLLWLPGARCADFVMTQTPASVSEPVGG

TVTIKCQASQSIYSYLSWYQQKPGQPPKLLIYGASTLASG

VPSRFKGSGSGTQFTLTISDLECADAATYYCQQGYTYTDI

DNVFGGGTEVVVK.
```

As demonstrated in the example below, the anti-asTF antibody is effective in decreasing cell proliferation induced by asTF in cells.

Other antibodies to asTF can be generated by standard techniques, using asTF. Since the proteins exhibit high evolutionary conservation, it may be advantageous to generate antibodies to the protein of a different species of origin than the species in which the antibodies are to be utilized, looking for those antibodies that are immunoreactive with the most evolutionarily conserved regions. Antibodies are typically generated by immunization of an animal using an adjuvant such as Freund's adjuvant in combination with an immunogenic amount of the protein administered over a period of weeks in two to three week intervals, then isolated from the serum, or used to make hybridomas that express the antibodies in culture. Because the methods for immunizing animals yield antibody that is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method may be used. Briefly, the variable region DNA of a selected animal recombinant anti-idiotypic ScFv is sequenced. Using this sequence, animal CDRs are distinguished from animal framework regions (FR) based on locations of the CDRs in known sequences of animal variable genes. Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) that incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA that codes for a flexible peptide. This assembly generates a single-chain Fv fragment (ScFv) that incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release delivery devices, as are well known in the art. The antibodies can also be administered with adjuvant, such as muramyl dipeptide or other materials approved for use in humans (Freund's adjuvant can be used for administration of antibody to animals). Antibodies can also be immobilized as discussed below.

Other compounds could also be identified or designed using standard techniques to specifically attenuate the asTF autocrine effect on cell proliferation. For example, medicinal chemistry is an interdisciplinary approach used to design small molecules, such as organic chemicals or peptides, for use as therapeutic agents. Medicinal chemists use a variety of technology platforms to discover and design drugs. These include combinatorial chemistry, computational chemistry, molecular modeling, high-throughput screening (HTS), enzymology, and pharmacology. The goal is to identify portions of a molecule responsible for particular activities, such as receptor binding or protein interaction. These properties can then be exploited to rationally design more effective drugs. Based on the structure and properties of a lead drug candidate, combinatorial chemists synthesize a series of closely-related analogs. Computational chemistry tools are then used to simulate the interactions of structural elements with macro-molecules, such as receptors, in order to correlate structure with activity. Scientists need to be able to predict function based upon structural elements. Computational chemistry tools include tools for 3-D structure analysis, quantitative structure-activity relationship analysis, and comparative molecular field analysis, among others. Several companies market software and services to help speed drug discovery and lead optimization programs.

The autocrine effects of asTF can be attenuated with methods that decrease the transcription of the primary TF RNA molecule or its splicing into the mature matrix RNA (mRNA) encoding asTF, or decrease the translation of the mRNA encoding asTF. For example, antisense that binds to the regulatory sequences, and/or to the protein encoding sequences can be synthesized using standard oligonucleotide synthetic chemistry. In the alternative, nucleic acids encoding the desired antisense sequence can be introduced to a cell via routine methods such as with expression vectors to cause the cell to generate the desired antisense sequence. The nucleic acids can be stabilized for pharmaceutical use using standard methodology such as encapsulation in a liposome or microsphere; introduction of modified nucleotides that are resistant to degradation or groups which increase resistance to endonucleases, such as phosphorothiodates and methylation, then screened initially for alteration of asTF activity in transfected or naturally occurring cells which express asTF, then in vivo in laboratory animals. Typically, the antisense would inhibit expression. However, sequences which block those sequences which "turn off" synthesis can also be targeted.

A pharmaceutical formulation that includes compounds that attenuate the autocrine effects of asTF are generally administered at a dose sufficient to attenuate the autocrine effects of asTF on asTF-induced cell proliferation. The dosage may vary depending on the route of administration, the type of compound being administered, and the physical characteristics of the subject such as age, health, weight, and sex. Generally, the pharmaceutical composition is administered such that the dose of the compound that attenuates asTF activity is administered in a dose having a range between about 0.1 ug/kg body to about 10 mg/kg body weight. In an embodiment, the pharmaceutical formulation may be administered directly into or local to a mass of proliferating cells. In an alternative embodiment, the pharmaceutical formulation may be administered systemically. In vitro studies indicate that a dose of 50 μg/ml of anti-asTF antibody is sufficient to inhibit cell proliferation. In vivo studies in mice indicate that about 100 μg/30 g mouse co-injected with tumor cells is adequate to inhibit asTF induced tumor growth. Thus, in an embodiment, an asTF inhibiting compound is administered at a dose in the range of about 3 mg/kg body weight to about 12 mg/kg body weight. In another embodiment, an asTF inhibiting compound is administered directly into or proximally to a mass of proliferating cells at a concentration of about 50 μg/ml to about 250 μg/ml.

The pharmaceutical composition may include other cancer fighting agents or may be coadministered with other cancer fighting agents known in the art, for example trastuzumab (Herceptin) as adjuvant treatment for breast cancer as a single agent within three weeks following completion of multi-modality, anthracycline-based chemotherapy regimens: initial dose at 8 mg/kg as an intravenous infusion over 90 minutes, and subsequent doses at 6 mg/kg as an intravenous infusion over 30-90 minutes every three weeks.

Compounds that alter asTF protein activity and/or binding (referred to generally herein as "binding activity") are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, Pluronic™, BASF).

Alternatively, the compound may be administered in liposomes or microspheres (or microparticles). Methods for preparing liposomes and microspheres for administration to a patient are known to those skilled in the art. Briefly, the material is dissolved in an aqueous solution, the appropriate phospholipids and lipids added, along with surfactants if required, and the material dialyzed or sonicated, as necessary. Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months.

Example

To explore whether asTF and flTF differentially contribute to breast cancer progression, analyzed asTF and flTF protein expression in a breast cancer tissue array (TA)

comprising specimens from 574 breast cancer patients was analyzed. Expression of asTF and flTF were detectable in >95% of the breast cancer samples, specimens with various degree of tumor cell positivity. Healthy mammary tissue showed far more limited expression of asTF compared to flTF (asTF: 4% of all specimens, flTF: 38%). Specificity of previously validated flTF- and asTF-specific antibodies was re-confirmed. Confocal analysis revealed flTF localization at the cell membrane, while asTF was mostly in the cytoplasmic vesicular structures.

Figure 1A:
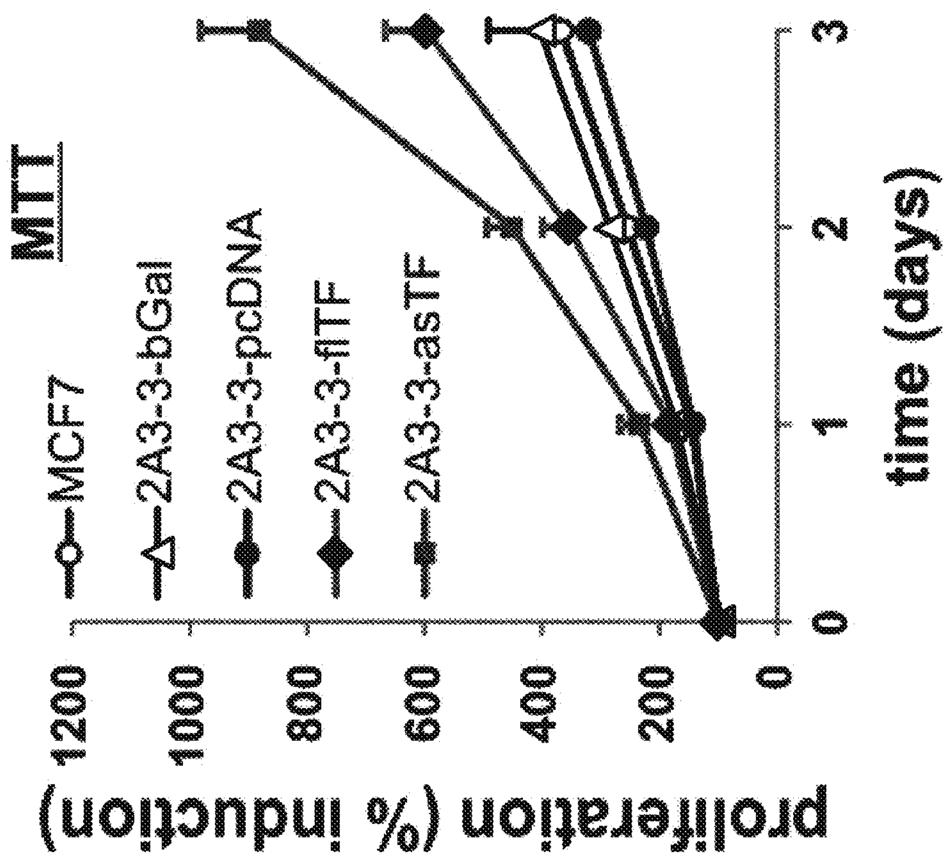
FIG. 1A is graph illustrating asTF induced cell proliferation.

Expression of asTF positively correlated with histological grade as well as tumor size (Table 1). In contrast, flTF expression only correlated with grade. No significant associations were found between asTF or flTF levels and ER, PgR, or HER2 status. These results raise the possibility that asTF impacts breast cancer progression in a manner qualitatively distinct from that of flTF.

further studies. Insertion of asTF and flTF cDNA resulted in similar mRNA expression levels, although intracellular protein levels of asTF were lower, likely due to asTF secretion (see below and FIG. 1F). Confocal analysis revealed that flTF was predominantly localized on the plasma membrane, while asTF was present in vesicular structures. Only 2A3-3 cells expressing flTF exhibited significant coagulant activity. 2A3-3 cells expressing flTF, asTF, an aspecific protein (β-Galactosidase), or empty vector control cells (pcDNA) were tested in an MTT proliferation assay and compared with parental MCF-7 cells. 2A3-3-pcDNA and 2A3-3-βGal proliferation rates were identical to those of MCF-7 (FIG. 1A). In contrast, proliferation rates of 2A3-3-asTF cells were increased by ≥2-fold, while those of 2A3-3-flTF cells were only modestly increased. Cell counting and genomic DNA measurements confirmed these results. An independently established second 2A3-3-asTF line showed similar

TABLE 1

| | Total N (%) | asTF − N (%)* | asTF + N (%)* | P | flTF − N (%)* | flTF + N (%)* | P |
|---|---|---|---|---|---|---|---|
| Total | 574 (100) | 119 (100) | 328 (100) | | 157 (100) | 351 (100) | |
| Age | | | | | | | |
| <40 | 48 (8.4) | 5 (4.2) | 26 (7.9) | 0.03 | 15 (9.6) | 26 (7.4) | 0.71 |
| 40-60 | 277 (48.3) | 72 (60.5) | 153 (46.6) | | 75 (47.8) | 171 (48.7) | |
| >=60 | 249 (43.4) | 42 (35.3) | 149 (45.4) | | 67 (42.7) | 154 (43.9) | |
| Missing* | 0 (0.0) | 0 (0.0) | 0 (0.0) | | 0 (0.0) | 0 (0.0) | |
| Grade | | | | | | | |
| I | 81 (14.1) | 26 (21.8) | 28 (8.5) | <0.001 | 30 (19.1) | 41 (11.7) | <0.001 |
| II | 282 (49.1) | 58 (48.7) | 159 (48.5) | | 88 (56.1) | 157 (44.7) | |
| III | 203 (35.4) | 33 (27.7) | 138 (42.1) | | 35 (22.3) | 149 (42.5) | |
| Missing* | 8 (1.4) | 2 (1.7) | 3 (0.9) | | 4 (2.5) | 4 (1.1) | |
| Histotype | | | | | | | |
| Ductal | 514 (89.5) | 104 (87.4) | 300 (91.5) | 0.39 | 133 (84.7) | 320 (91.2) | 0.065 |
| Lobular | 53 (9.2) | 13 (10.9) | 25 (7.6) | | 20 (12.7) | 27 (7.7) | |
| Missing* | 7 (1.2) | 2 (1.7) | 3 (0.9) | | 4 (2.5) | 4 (1.1) | |
| T status | | | | | | | |
| T1 | 211 (36.8) | 56 (47.1) | 97 (29.6) | 0.002 | 64 (40.8) | 120 (34.2) | 0.26 |
| T2 | 272 (47.4) | 46 (38.7) | 173 (52.7) | | 71 (45.2) | 171 (48.7) | |
| T3-4 | 72 (12.5) | 13 (10.9) | 49 (14.9) | | 17 (10.8) | 51 (14.5) | |
| Missing* | 19 (3.3) | 4 (3.4) | 9 (2.7) | | 5 (3.2) | 9 (2.6) | |
| N status | | | | | | | |
| N0 | 307 (53.5) | 64 (53.8) | 166 (50.6) | 0.62 | 93 (59.2) | 182 (51.9) | 0.18 |
| N1-3 | 250 (43.6) | 53 (44.5) | 153 (46.7) | | 62 (39.5) | 158 (45.0) | |
| Missing* | 17 (3.0) | 2 (1.7) | 9 (2.7) | | 2 (1.3) | 11 (3.1) | |
| ER status | | | | | | | |
| Negative | 208 (36.2) | 37 (31.1) | 124 (37.8) | 0.17 | 54 (34.4) | 123 (35.0) | 0.96 |
| Positive | 344 (59.9) | 79 (66.4) | 193 (58.8) | | 93 (59.2) | 214 (61.0) | |
| Missing* | 22 (3.8) | 3 (2.5) | 11 (3.4) | | 10 (6.4) | 14 (4.0) | |
| PgR status | | | | | | | |
| Negative | 234 (40.8) | 40 (33.6) | 136 (41.4) | 0.10 | 50 (31.8) | 144 (41.0) | 0.06 |
| Positive | 311 (54.2) | 77 (64.7) | 181 (55.2) | | 97 (61.8) | 191 (54.4) | |
| Missing* | 29 (5.1) | 2 (1.7) | 11 (3.4) | | 10 (6.4) | 16 (4.6) | |
| HER2** | | | | | | | |
| Negative | 406 (70.7) | 86 (72.3) | 236 (71.9) | 0.14 | 105 (66.9) | 244 (69.5) | 0.28 |
| Positive | 50 (8.7) | 6 (5.0) | 32 (9.8) | | 9 (5.7) | 32 (9.1) | |
| Missing* | 118 (20.6) | 27 (22.7) | 60 (18.3) | | 43 (27.4) | 75 (21.4) | |

asTF Expression Enhances Proliferation of Breast Cancer Cells

Figures 1C, 1D:
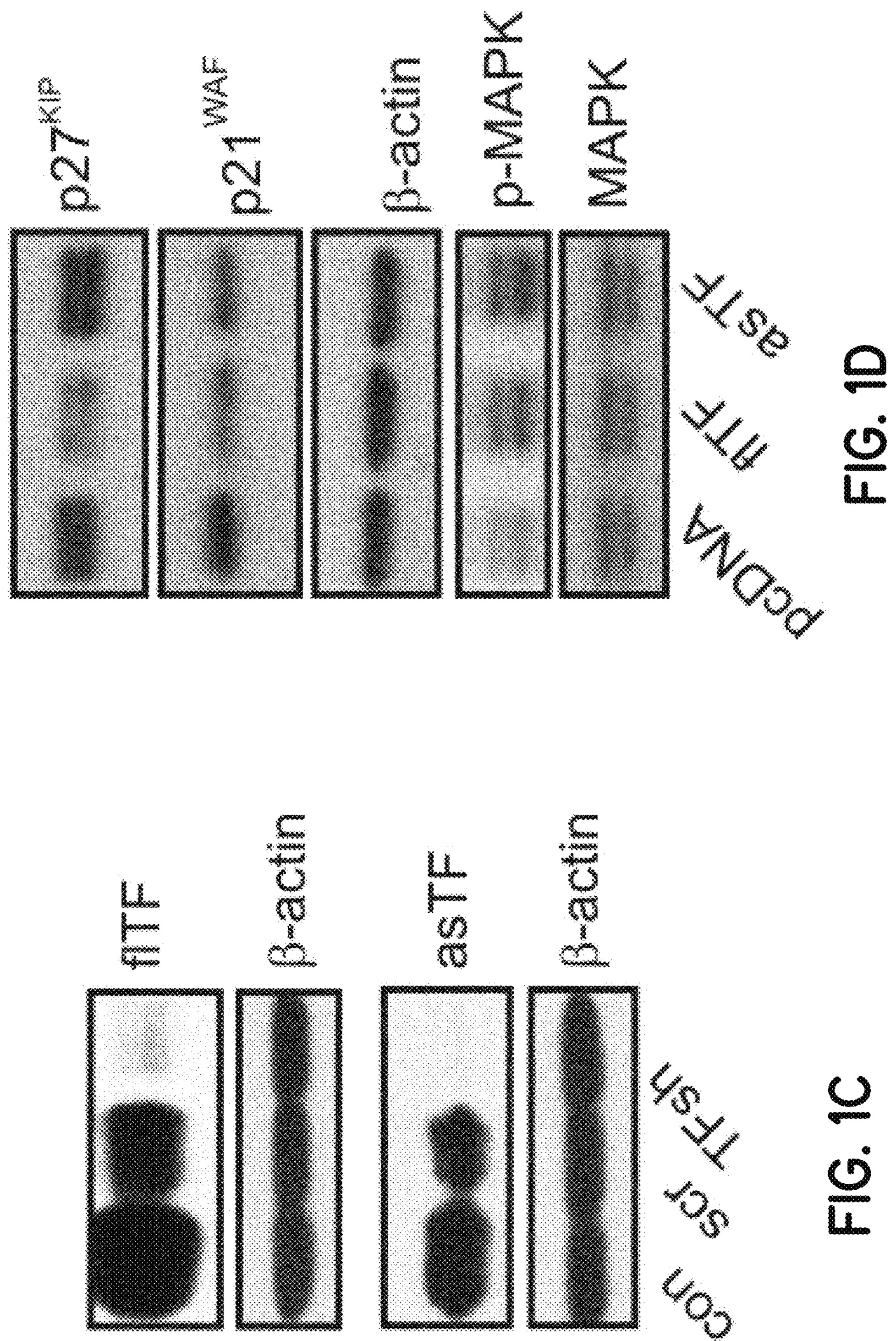
FIG. 1C is graph illustrating asTF induced cell proliferation.
FIG. 1D is a representative blot of asTF and flTF expression in cells transduced with asTF and flTF constructs.
Figures 1E, 1F:
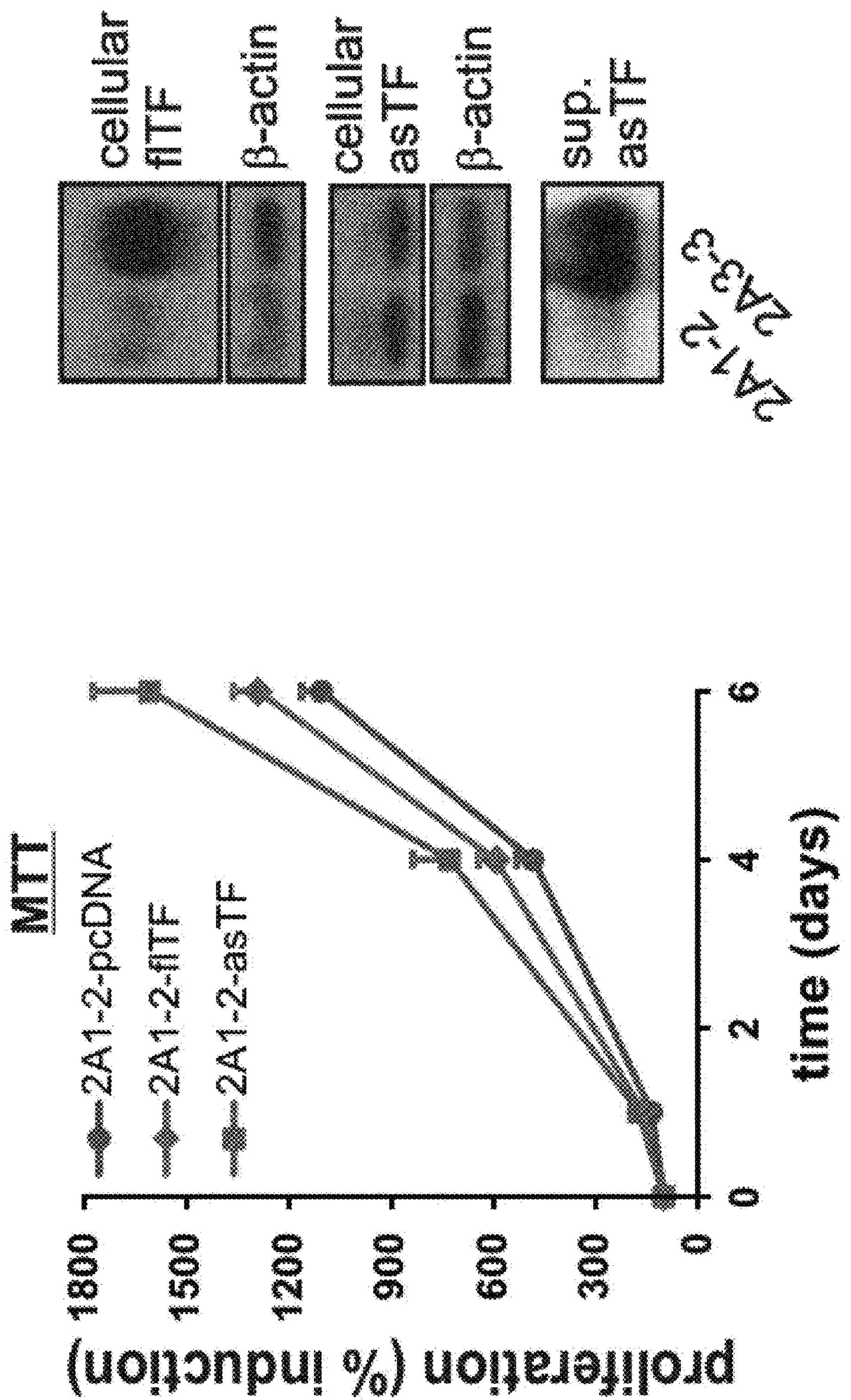
FIG. 1E is a representative blot of cell cycle inhibitors and MAP kinase phosphorylation in cells transduced with asTF and flTF constructs.
FIG. 1F is a representative blot of cell cycle inhibitors and MAP kinase phosphorylation in cells transduced with asTF and flTF constructs.
Figure 1H:
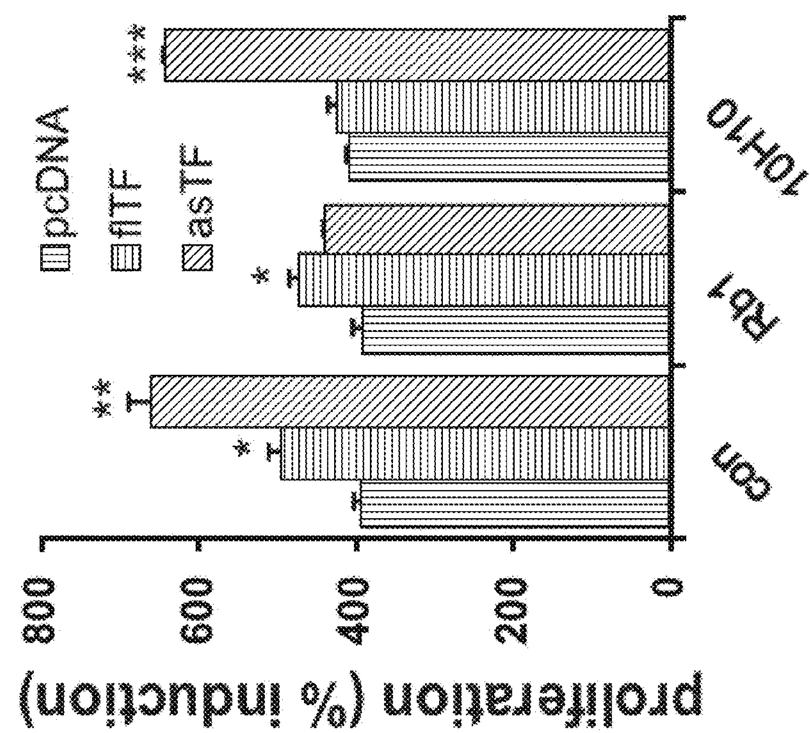
FIG. 1H is bar graph illustrating asTF induced cell proliferation.
Figure 1G:
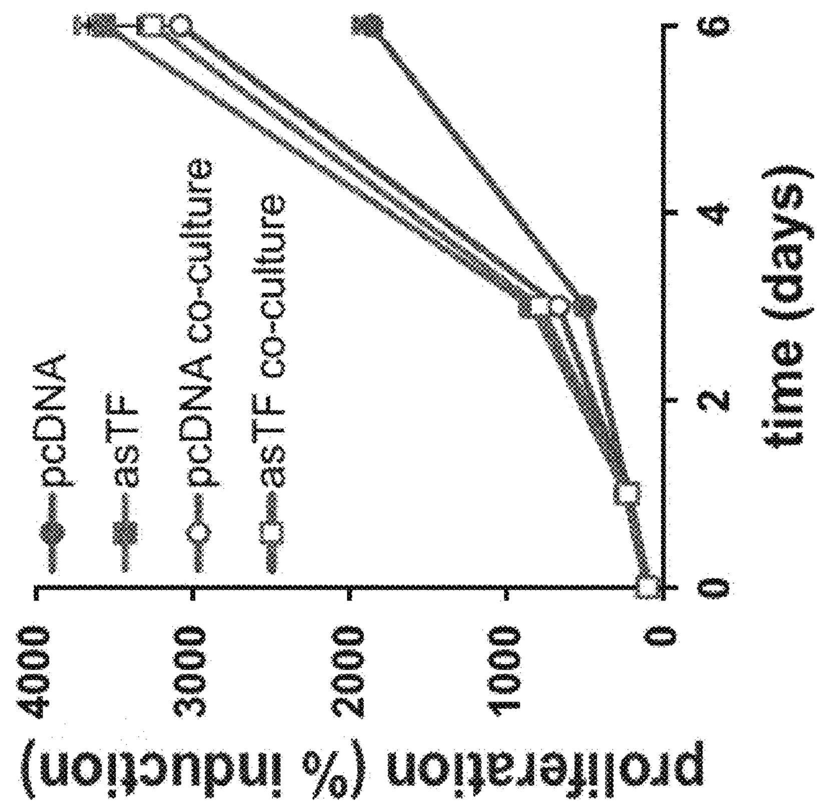
FIG. 1G is a is graph illustrating asTF induced cell proliferation.
Figure 2C:
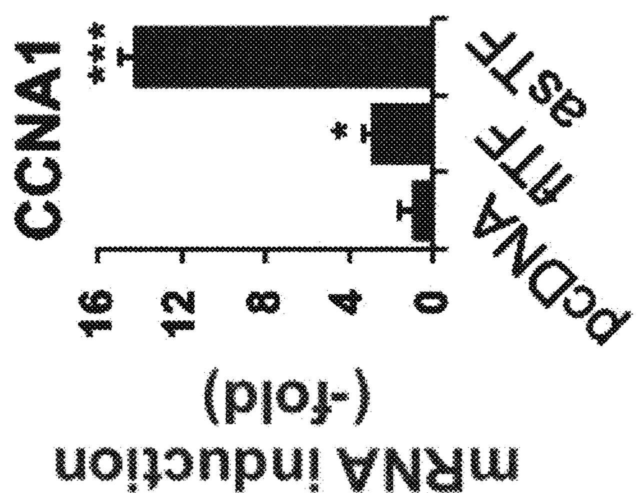
FIG. 2C is a bar graph illustrating induction of CCNA1 mRNA induced by asTF.
Figure 2B:
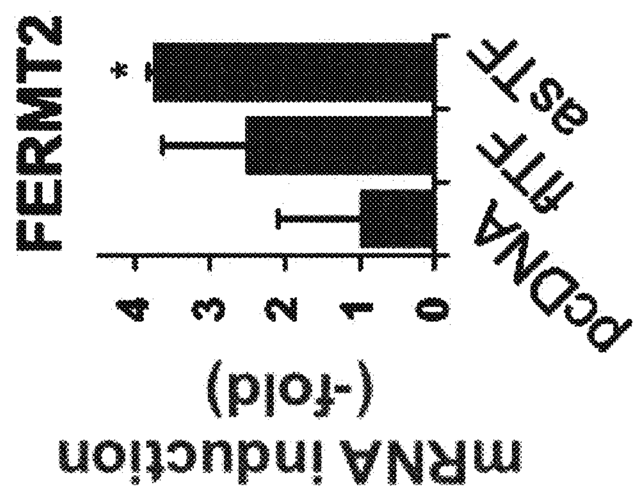
FIG. 2B is a bar graph illustrating induction of FERMT2 mRNA induced by asTF.
Figure 2A:
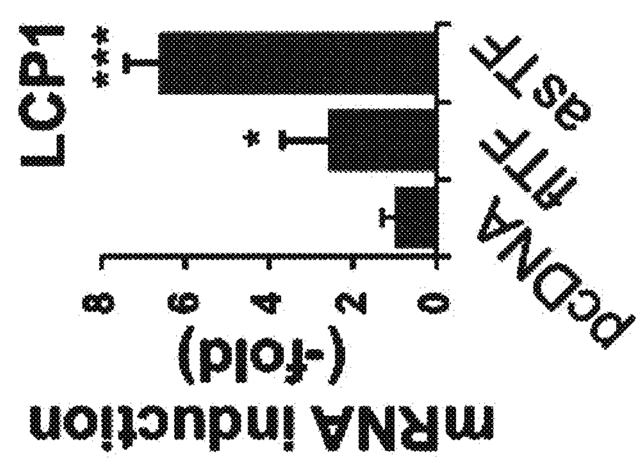
FIG. 2A is a bar graph illustrating induction of LCP1 mRNA induced by asTF.
Figure 2F:
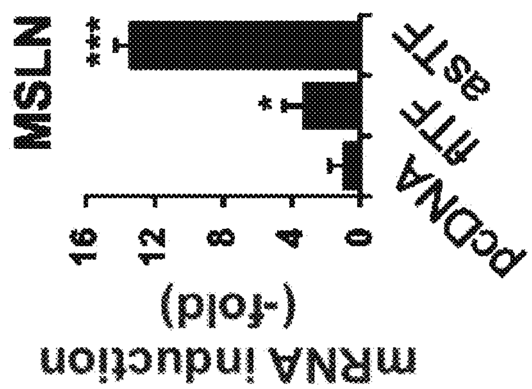
FIG. 2F is a bar graph illustrating induction of MSLN mRNA induced by asTF.
Figure 2E:
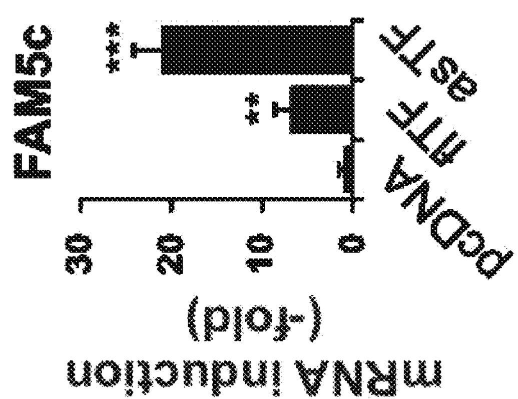
FIG. 2E is a bar graph illustrating induction of FMA5c mRNA induced by asTF.
Figure 2D:
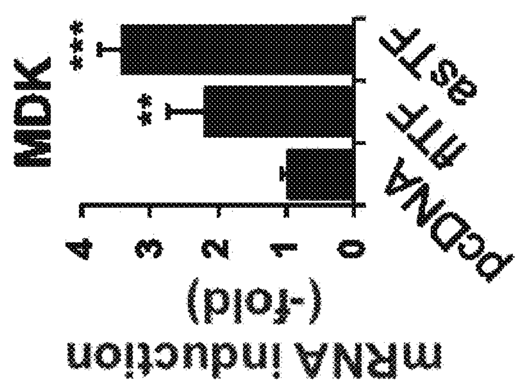
FIG. 2D is a bar graph illustrating induction of MDK mRNA induced by asTF.
Figure 2I:
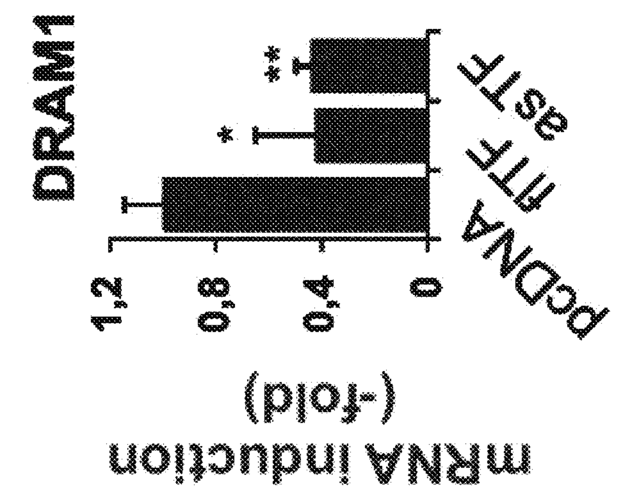
FIG. 2I is a bar graph illustrating induction of DRAM1 mRNA induced by asTF.
Figure 2H:
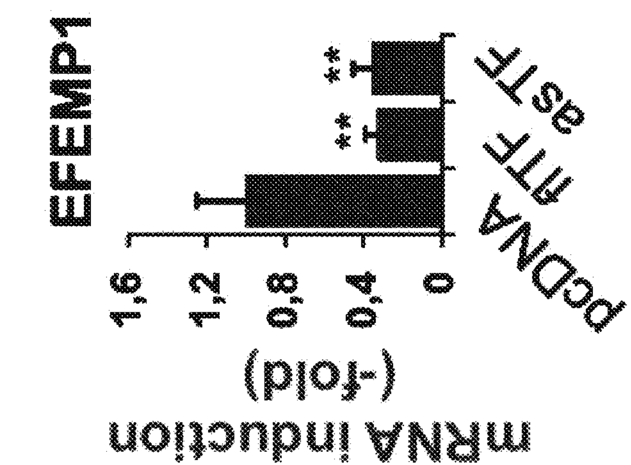
FIG. 2H is a bar graph illustrating induction of EFEMP1 mRNA induced by asTF.
Figure 2G:
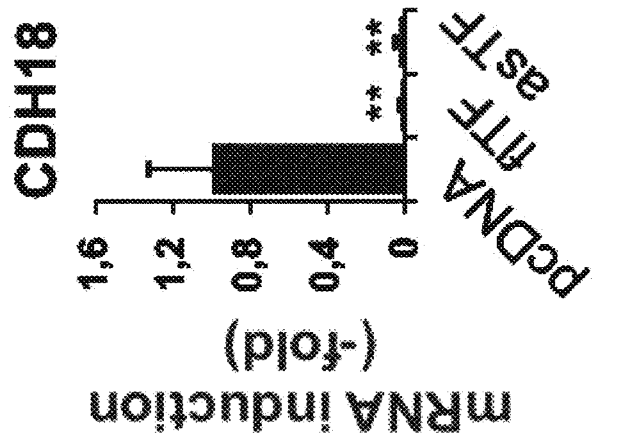
FIG. 2G is a bar graph illustrating induction of CDH18 mRNA induced by asTF.

It was not previously known whether asTF can exert autocrine effects on cancer cells. To explore the mechanistic link between the unique correlation of asTF expression and breast cancer clinical parameters, MCF-7 cells were constructed that harbored a genomic FRT insertion and several FRT lines were established. Clone 2A3-3 was selected for proliferation rates and TF-specific shRNA eliminated enhanced proliferation (FIGS. 1B, 1C), confirming that the effect was asTF-dependent. Increased cell numbers were not due to changes in cell survival, as all cell lines showed similar viability levels.

asTF and flTF expression resulted in down-regulation of cell cycle inhibitors and enhanced phosphorylation of the pro-mitogenic p42/p44 MAP kinase (FIG. 1F). The effects of flTF and asTF expression on cell proliferation were somewhat less pronounced in an MCF-7 FRT clone (2A1-2) with lower flTF/asTF expression (FIG. 1E, 1F). Of note, 2A1-2 cells exhibited decreased asTF secretion while cellular asTF levels were equal to those in 2A3-3 cells (FIG. 1F), suggesting that asTF secretion is critical to the enhancement of proliferation. Indeed, co-culture of control cells with asTF-expressing cells increased control cell proliferation (FIG. 1G). Culturing control cells in 2A3-3-asTF-conditioned medium enhanced proliferation, and asTF depletion from the medium reversed this effect. Addition of recombinant asTF to control cells that do not express either TF isoform, increased proliferation in a concentration-dependent manner. Incubation of asTF-expressing 2A3-3 cells with an asTF-blocking antibody, but not with an flTF-blocking antibody, reduced asTF-dependent cell proliferation (FIG. 1H). Limited flTF-elicited proliferation was not dependent on PAR2 activation, as incubation with PAR2- and FVII-blocking antibodies was without effect. Together, these results demonstrate that secreted asTF enhances breast cancer cell proliferation in an autocrine fashion.

asTF Augments Pro-Oncogenic Gene Expression

Next, the gene expression profiles in asTF-expressing 2A3-3 cells were compared with those in control or flTF expressing 2A3-3 cells. Compared to control or flTF expressing cells, asTF expression upregulated genes involved in cell cycle progression (e.g. CCNA1), tumor proliferation (e.g. MDK), cytoskeletal reorganization/motility (e.g. FERMT2), invasion (e.g. FAM5c), and cell survival (e.g. MSLN) (FIGS. 2A-2I). Moreover, expression of asTF downregulated several tumor suppressors (e.g. CDH18), and genes involved in cell cycle arrest (e.g. EFEMP1) and apoptosis (DRAM1) (FIGS. 2A-2I). Expression of SRPK2 that phosphorylates and activates the major TF pre-mRNA splicing regulator ASF/SF2 was altered by asTF as well as flTF, suggesting that TF splice variants regulate their own expression. These results indicate that asTF enhances breast cancer cell proliferation via modulation of cell cycle regulators, proliferation inducers, and tumor suppressors/pro-apoptotic proteins.

asTF Enhances Proliferation by Binding to a Non-Canonical Site on β1 Integrins

As we previously showed that asTF can induce angiogenesis via binding integrins on endothelial cells (EC), we reasoned that asTF-dependent breast cancer cell proliferation may likewise be integrin-dependent. shRNA-mediated silencing of the β1 integrin subunit resulted in diminished proliferation of 2A3-3-asTF cells (FIGS. 3A, 3C) and flTF cells, but not control cells; shRNA against the β3 integrin subunit, which is not expressed in these cells, was without effect.

Figure 3B:
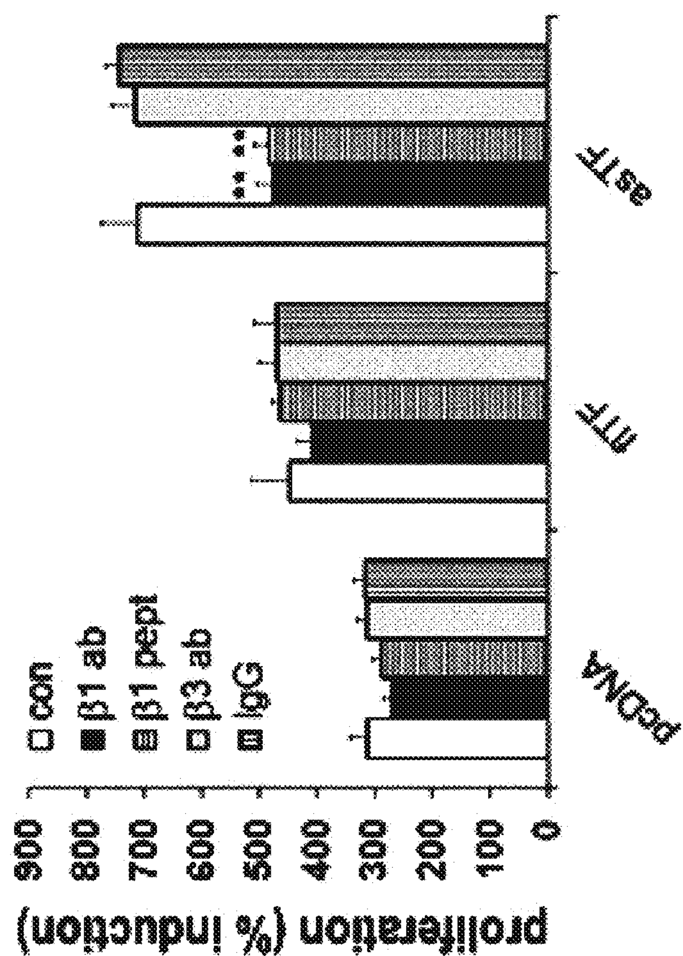
FIG. 3B is a bar graph illustrating the effect of β1 integrin blockade on asTF induced proliferation.
Figure 3A:
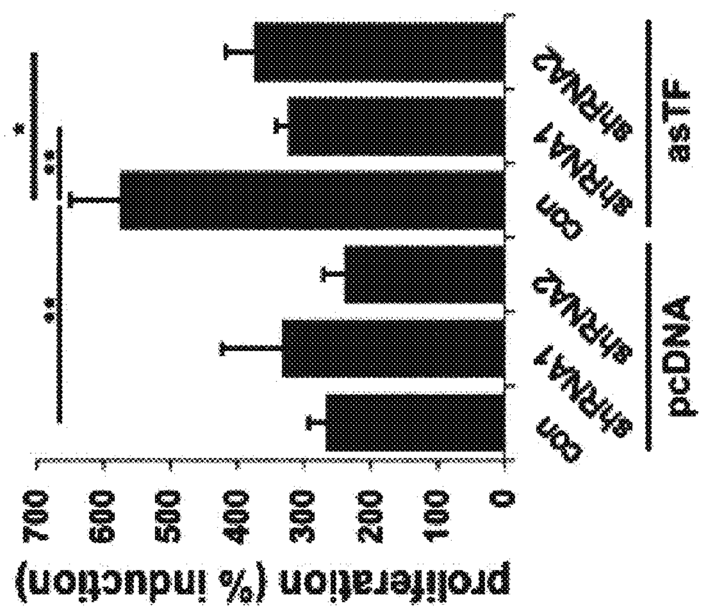
FIG. 3A is a bar graph illustrating the effect of shRNA silencing of β1 integrin on asTF induced proliferation.
Figure 3E:
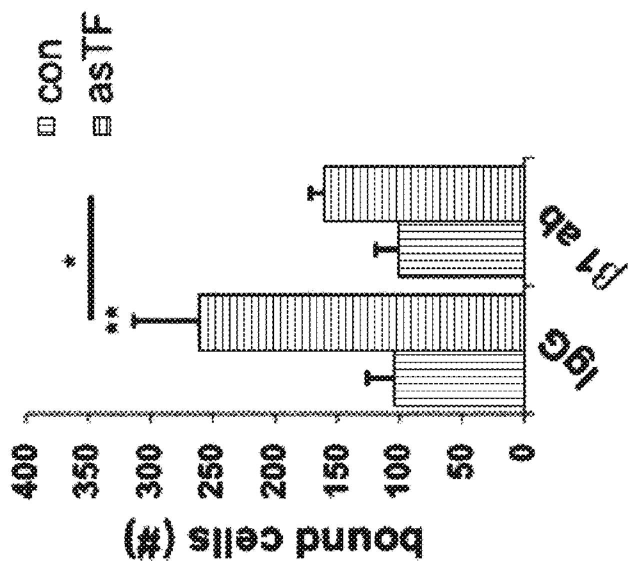
FIG. 3E is a bar graph illustrating that β1 integrin antibody blocks asTF induced cell adhesion.
Figure 3D:
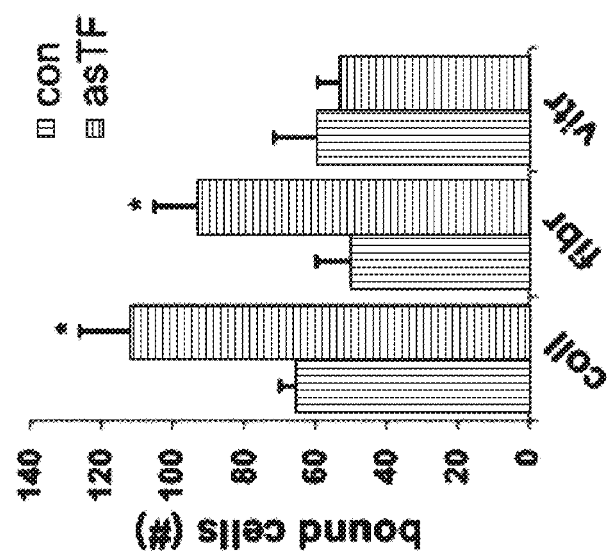
FIG. 3D is a bar graph illustrating the effect of asTF on cell adhesion.
Figure 3C:
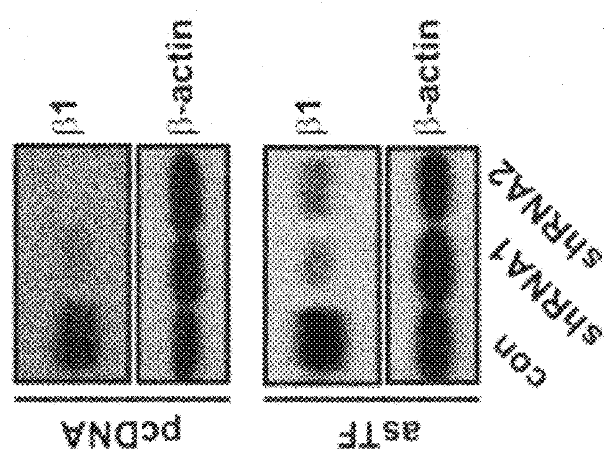
FIG. 3C is a representative blot showing β1 integrin protein levels in cells treated with lentiviral β1 constructs.

Artificially truncated recombinant flTF (sTF) was recently found to induce EC proliferation by binding to the integrin β1 region between residues 579 and 799. Because sTF contains the entire asTF N-terminal region, we decided to test whether asTF binds to this integrin region. An antibody against the β1 aa 579-799 domain and a peptide resembling this domain inhibited proliferation of 2A3-3-asTF cells, but not control cells (FIG. 3B). Neither the antibody nor the peptide was able to reverse flTF-dependent proliferation, even after prolonged incubation (FIG. 3B). Pre-incubation of control cells in suspension with recombinant asTF enhanced cell binding to collagen and fibronectin, but not vitronectin (FIG. 3D), suggesting that asTF binding modulates integrin activation. Again, functional blockade of β1 (FIG. 3E) but not β3 (not shown), reversed this effect. In support of an activating effect of asTF on β1 integrins, reactivity of HUTS-21, an antibody that recognizes the active conformation of β1 integrins, increased when 2A3-3 cells expressed asTF or were exposed to recombinant asTF. To ascertain asTF co-localization with β1 integrins, we pre-incubated control cells with fluorescently-tagged recombinant asTF; partial co-localized with β1 integrins on the cell surface was observed. As β1 integrin blockade in 2A3-3 cells only partially inhibited asTF-dependent proliferation, these results suggest that, aside from β1 integrins, asTF likely binds to other membrane-associated proteins.

asTF Induces Anchorage-Independence and Tumor Growth In Vivo

Figure 4A:
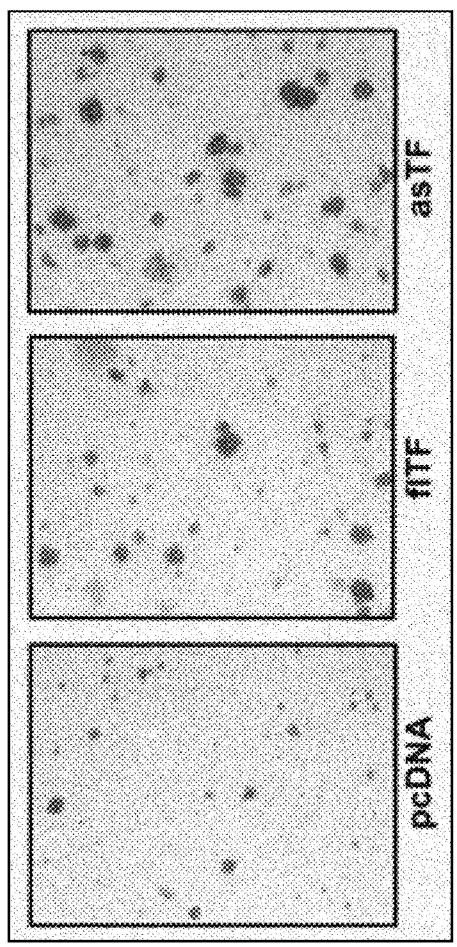
FIG. 4A is a photomicrograph of transformed cell cultures.
Figure 4B:
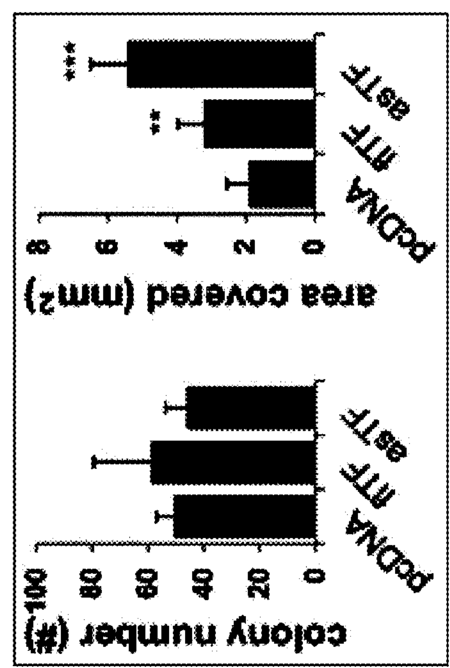
FIG. 4B is a bar graph illustrating asTF induced cell proliferation of transformed cells.
Figure 4D:
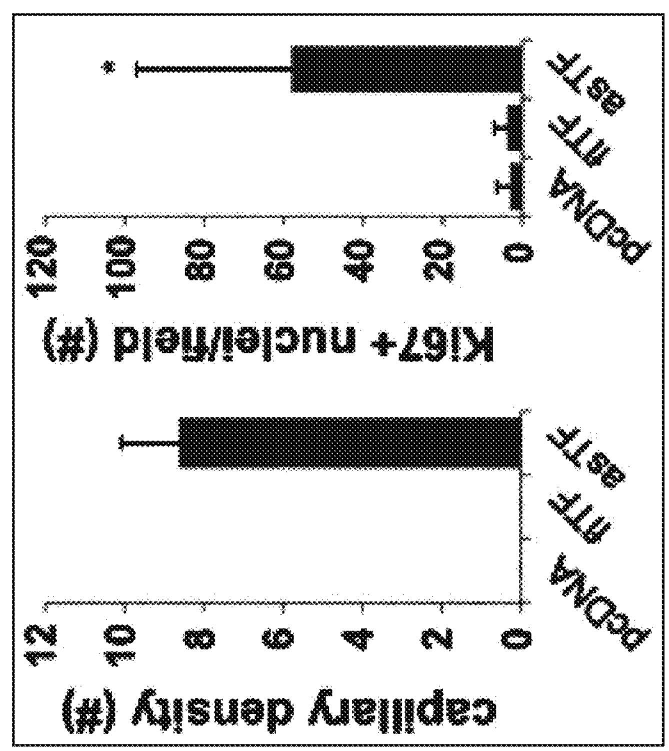
FIG. 4D is a bar graph illustrating the effect of asTF on capillary density macrophage infiltration.
Figure 4C:
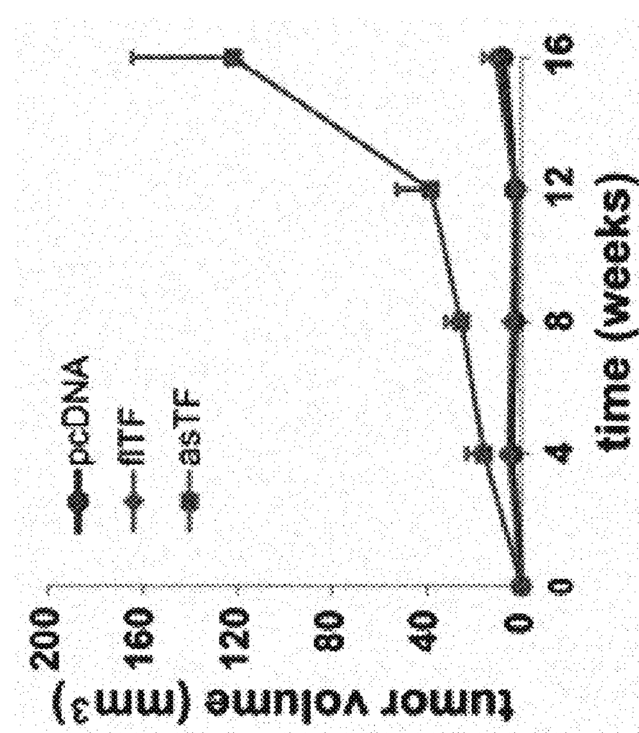
FIG. 4C is a graph illustrating the increase in tumor size induced by transformed cells injected into the fad pad of NOD-SCID mice.

The effects of asTF expression on the oncogenic potential using a soft-agar assay was also investigated. While asTF did not affect the number of colonies, it caused a 3-fold increase in colony size; the impact of flTF expression on colony size was marginal (FIGS. 4A-4B).

asTF-dependent tumor growth was then assessed orthotopically. Compared to control, asTF expression severely increased tumor expansion (FIG. 4C). In contrast, flTF-expressing 2A3-3 cells yielded tumors that were similar in size or smaller than those formed by control cells. asTF-expressing cells yielded massive tumors with little stroma, whereas control and flTF cells gave rise to small tumor islands surrounded by stroma. flTF and asTF expression was confirmed in tumors in vivo, ruling out that poor growth of flTF-expressing cells was due to loss of flTF expression. asTF-expressing tumors had more CD31+ capillaries and macrophage infiltrate, and contained more proliferating tumor cells, specifically at the tumor periphery. (FIG. 4D). These data demonstrate that asTF promotes breast cancer cell proliferation in vitro and in vivo.

asTF Blockade Reduces Growth of Breast Cancer Cells Expressing Endogenous asTF

Figure 5C:
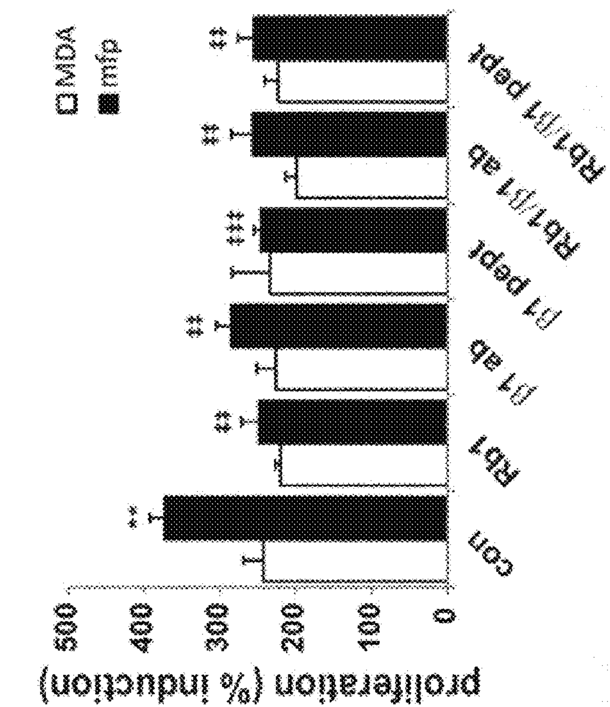
FIG. 5C. is a bar graph illustrating the inhibition of proliferation by incubation with an anti-asTF antibody (Rb1), β1 integrin peptide, combination Rb1 and β1 integrin antibody, and combination Rb1 and β1 integrin peptide.
Figure 5B:
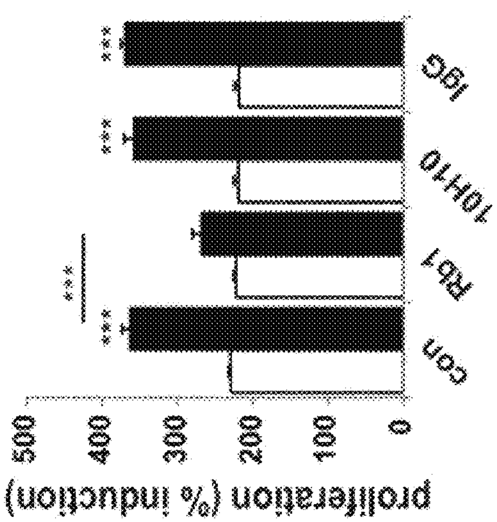
FIG. 5B is a bar graph illustrating the inhibition of proliferation by incubation with an anti-asTF antibody.
Figure 5A:
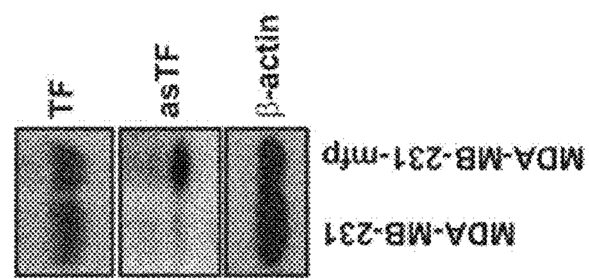
FIG. 5A is a blot showing asTF expression in MDA-MB-231 and MDA-MB-231-mfp cells.

While the role of asTF in tumor growth was dissected using MCF-7 cells constructed to exclusively express either asTF or flTF, native asTF is co-expressed with flTF. Moreover, MCF-7 cells express low levels of PAR2, which may mechanistically explain the lack of 2A3-3-flTF-dependent tumor expansion in vivo. Because MDA-MB-231 breast cancer cells express high levels of flTF and PAR2, we employed them to assess the role of asTF in an flTF/PAR2-positive setting. Although asTF levels in MDA-MB-231 cells were low (FIG. 5A), a more aggressive MDA-MB-231 sub-line that had been isolated from the mammary fat pad following orthotopic implantation (MDA-MB-231-mfp) had significantly higher asTF levels, while flTF levels were unchanged. In agreement, spliceosomal proteins that promote biosynthesis of asTF mRNA were upregulated in MDA-MB-231-mfp cells. asTF-specific antibody blockade significantly inhibited proliferation of MDA-MB-231-mfp cells (FIG. 5B). asTF blockade did not have an effect on proliferation of the parental MDA-MB-231 line, demonstrating functional specificity. Anti-flTF antibody 10H10 did not inhibit proliferation of either cell type in vitro, which is consistent with the notion that flTF potentiates angiogenesis—but not proliferation—in these cells (FIG. 5B). A β1 integrin-blocking antibody or the aa 579-799 integrin peptide also inhibited proliferation of MDA-MB-231-mfp cells, but did not further reduce proliferation in the presence of the anti-asTF antibody (FIG. 5C), confirming that asTF augments proliferation in MDA-MB-231-mfp via β1 integrins. β3 integrin blockade was without effect (FIG. 5D).

MDA-MB-231-mfp cells were orthotopically implanted in NOD-SCID gamma (NSG) mice in the presence or absence of asTF-blocking antibody. asTF blockade with as little as 100 μg antibody significantly stemmed tumor growth (FIG. 5E) and resulted in a marked reduction of the proliferation zone at the tumor periphery (FIG. 5F). asTF blockade did not reduce vascular density, suggesting that asTF does not impact angiogenesis in a model featuring a pro-angiogenic flTF-PAR2 axis (FIG. 5G. Thus, asTF blockade downregulates the tumorigenic potential of breast cancer cells expressing native asTF, flTF, and PAR2.

Until now, contributions of asTF to tumor progression have remained unclear. This is the first study that documents asTF's selective abundance in breast cancer tissue, and demonstrates that asTF profoundly impacts breast cancer progression by inducing breast cancer cell proliferation in an autocrine manner. This is also the first report to assess efficacy of anti-asTF monoclonal antibodies. Analysis of asTF and flTF expression in breast cancer specimens from 574 patients revealed that asTF positively correlates with both grade and the T-status of cancer lesions, while flTF positively correlates solely with tumor grade, and is detectable in ~40% of normal breast tissue, compared to ~4% for asTF. These data demonstrate for the first time that asTF upregulates breast cancer cell proliferation irrespective of its impact on angiogenesis in a model constructed to overexpress asTF, as well as in breast cancer cells that express native asTF. The effects of flTF expression pale in comparison with asTF-triggered potentiation of proliferation; further, flTF-dependent proliferation was not observed in an aggressive MDA-MB-231 cell line that expresses asTF. Thus, asTF is the major TF variant that promotes proliferation of breast cancer cells.

asTF upregulated genes that play pivotal roles in cell cycle progression and proliferation. CNNA1 and CNNA2, important regulators of cyclin-dependent kinases during S phase, and ANAPC10 were significantly upregulated in 2A3-3-asTF cells compared to control or flTF expressing cells. Growth factors (MDK, GAL and TIMP1) were also upregulated. Although we observed upregulation of some cell survival genes, we found no evidence for altered cell survival in asTF-expressing cells. Still, it cannot be ruled out that these genes contribute to the cumulative impact of asTF expression on tumor xenografts.

These studies further revealed that asTF-integrin interactions were responsible for increased proliferation of MDA-MB-231-mfp cells. asTF co-localized with β1 integrins on the cell surface, and β1 integrin silencing reversed asTF-dependent proliferation. Blocking experiments using an antibody against the β1 region encompassing residues 579-799 or a peptide resembling this domain, reversed asTF-dependent—but not flTF-dependent—proliferation, suggesting that asTF binds to this distinct β1 region. The finding that asTF, the naturally occurring soluble TF variant, induces proliferation via integrin binding is without precedent. It is posited that asTF induces a conformational change in β1 integrins that render them prone to activation, a β1 integrin-blocking antibody was used that is reactive with the membrane-proximal f3-tail domain (βTD) of the β1 integrin subunit, and the 579-799 integrin peptide features this domain. The βTD contains a CD-loop that contacts the ligand-binding integrin βA domain and the hybrid domain, and this contact is lost upon integrin activation. Therefore, it has been postulated that the CD-loop acts as a deadbolt, preventing integrin activation by locking βA in an inactive state. Indeed, a number of antibodies that activate β1 integrins bind to the βTD or the βA interface, and the βTD has been shown to regulate ligand binding. The data suggest that asTF induces removal of the CD-loop deadbolt. However, direct conformational effects of asTF on the function of β1 integrins are not likely to be the sole means by which asTF modulates the "integrin profile" of breast cancer cells, because asTF expression also upregulates kindlin-2, a positive regulator of talin-induced integrin activation, and suppresses tensin-3, a negative regulator of integrin function.

The in vitro phenotype of asTF-expressing 2A3-3 cells, i.e. enhanced proliferation and colony growth in soft agar, was recapitulated in vivo while flTF-expressing cells that proliferated only moderately faster than control cells in vitro, produced tumors of the same size as control cells in vivo. It is not entirely clear why flTF-expressing cells are incompetent in vivo, but the paucity of PAR2 expression may be a contributing factor. PAR2 is instrumental in flTF-dependent tumor angiogenesis, and poor expansion of these cells may result from a lack of PAR2-dependent angiogenesis. This is in agreement with the results of in vivo experiments employing PAR2-expressing MDA-MB-231-mfp cells to the effect that asTF blockade did not affect vascular development in tumor xenografts, although we did not directly test the influence of asTF-induced angiogenesis on breast cancer growth. These results indicate that asTF does not significantly influence angiogenesis in the MDA-MB-231-mfp xenograft model, while upregulation of CD31+ vessels in asTF-expressing 2A3-3 tumors suggests that asTF-dependent angiogenesis may be a significant contributing factor in 2A3-3 xenografts. Differences in secreted asTF levels and/or presence of a functional flTF-PAR2 axis in MDA-MB-231-mfp cells may explain why asTF differently affects vascular density in these two xenograft models.

SR protein-mediated alternative splicing has been deemed critical to the proliferation of breast cancer cells: overexpression of ASF/SF2, a major SR protein and regulator in the maintenance of the flTF/asTF mRNA ratio in monocytes, leads to enhanced cell proliferation, transformation, and breast cancer growth in vivo. Further, the expression of SRp40—the spliceosomal protein that promotes asTF biosynthesis, whose levels are upregulated in MDA-MB-231-mfp cells—is increased in human breast cancer, and associated with lymph node metastasis. It may be of interest to investigate whether the effects of heightened SRp40 expression in breast cancer are in part dependent on asTF production.

In conclusion, autocrine asTF expression induces integrin-mediated breast cancer cell proliferation that contributes to tumor growth, rendering asTF a novel target for anti-cancer strategies that selectively modulate the biological activity of this minimally coagulant TF form, thereby avoiding an adverse impact on hemostasis.

The following methods were used to collect the data for this Example. Cell proliferation was assessed using MTT assays with routine methods. In some experiments, outcomes of MTT assays were verified using cell counting and DNA analysis. In brief, cells were seeded in 10 cm dishes, lifted and counted at day 0 and day 3. Proliferation was expressed as an increase in cell number compared to the cell number at day 0. For DNA analysis, cells were lysed in SDS buffer at day 0 and day 3 and DNA contents were measured using Nanodrop. When appropriate, flTF- (10H10, 50 μg/ml), asTF- (RabMab1, 50 μg/ml), β1- and β3 integrin antibodies (50 μg/ml) or a β1 peptide (1 nM) were added. To measure apoptosis, cells were lifted, incubated with Annexin V/propidium iodide (both Sigma-Aldrich, St. Louis, Mo.) and measured by FACS (LSR2; Becton Dickinson, Franklin Lakes, N.J.).

For HUTS-21 staining, cells were fixed in ice-cold methanol for 5 minutes. In all other experiments, cells were fixed in 2% formaldehyde, permeabilized with 0.1% Triton-X100 when appropriate. Cells were incubated O/N with primary antibodies followed by incubation with secondary antibodies conjugated to Alexa-488 or Alexa-594. Coverslips were mounted using Vectashield containing DAPI (Vector Laboratories, Burlingame, Calif.). In some experiments, cells were incubated with fluorescently-conjugated asTF for 20 min, before fixation. Images were acquired using a Leica SP5 confocal microscope and a Leica DMI6000B.

For animal studies, 5 animals per experimental group were used. 2A3-3 cells ($2*10^6$ in 50 μl) were injected into the inguinal fat pad of NOD-SCID mice (Charles River, Maastricht, The Netherlands). Tumor growth was measured using calipers and the formula V=(l*w*w)/2, (V: tumor volume; l; tumor length; w: tumor width. For MDA-MB-231-mfp growth in vivo, $0.5*10^6$ cells were injected in fat pads of NOD-SCID-gamma mice (Charles River, Maastricht, The Netherlands). After completion, tumors were extracted and fixed in 4% formalin. Sections were deparaffinized, rehydrated, endogenous peroxidase activity was blocked with 0.3% $H_2O_2$. Antigen retrieval was done in sodium citrate buffer for 10 minutes at 100° C. Sections were blocked for 1 hour with 10% normal goat serum in PBS and incubated overnight at 4° C. with primary antibody. Sections were incubated for 30 minutes with Envision (Dako, Heverlee, Belgium), visualized using DAB, and counterstained with hematoxylin.

A tissue array was constructed from tumor material obtained from 574 non-metastasized breast cancer patients that mostly underwent tumor resection at Leiden University Medical Center between 1985 and 1994. Median follow-up was 17.9 years (range: 0.01 to 23.5). Age, tumor grade, histological type, TNM status, locoregional or distant tumor recurrence, and expression of estrogen receptor (ER), progesterone receptor (PgR), and human epidermal growth factor receptor 2 (HER2) were known. Tumors were graded according to the current pathological standards. Normal mammary tissue of 266 patients (46%) was available for analysis. Sections were cut and stained for flTF and asTF as described above. The percentage of asTF and flTF positive tumor cells was scored by two blinded observers. Patients in the 1st quartiles were deemed negative.

What is claimed is:

1. A method of inhibiting proliferation of a cell induced by alternatively spliced Tissue Factor ("asTF") comprising:

exposing the proliferating cell to an inhibitor of asTF at a concentration sufficient to attenuate asTF induced proliferation, wherein the inhibitor is a monoclonal anti-asTF antibody raised against a peptide sequence having SEQ ID NO: 1 and includes a first variable sequence having SEQ ID NO: 2 and a second variable sequence having SEQ ID NO: 3, and the antibody interrupts interaction of asTF with β-integrin to attenuate cellular proliferation.

2. The method of claim 1 wherein the cell is a cancer cell.

3. The method of claim 1 wherein the cell is a breast cancer cell.

4. The method of claim 1 wherein the cell expresses asTF.

5. The method of claim 1 wherein the anti-asTF antibody is a fragment of an antibody.

6. A method of treating a proliferating cell disorder in a subject comprising:

administering an inhibitor of asTF to the subject at a dose sufficient to inhibit cell proliferation, wherein the inhibitor is a monoclonal anti-asTF antibody raised against a peptide sequence having SEQ ID NO: 1 and includes a first variable sequence having SEQ ID NO: 2 and a second variable sequence having SEQ ID NO: 3, and the antibody interrupts interaction of asTF with β-integrin to attenuate cellular proliferation.

7. The method of claim 6 wherein the proliferating cell is a cancer cell.

8. The method of claim 7 wherein the cancer cell is a breast cancer cell.

9. The method of claim 6 wherein the anti-asTF antibody is a fragment of an antibody.

10. The method of claim 1 wherein the anti-asTF antibody is a humanized antibody.

11. The method of claim 6 wherein the anti-asTF antibody is a humanized antibody.

* * * * *